United States Patent [19]
Gammell

[11] Patent Number: 5,532,589
[45] Date of Patent: Jul. 2, 1996

[54] SUBSURFACE EXAMINATION OF NON-FERROUS MATERIAL FOR DETECTING CORROSION BY MEASURING MAGNETIC TRACTION

[75] Inventor: Paul M. Gammell, Silver Spring, Md.

[73] Assignee: The United States of America as represented by the Secretary of the Navy, Washington, D.C.

[21] Appl. No.: 450,774

[22] Filed: May 24, 1995

[51] Int. Cl.⁶ .......................... G01N 27/82; G01N 17/00; G01N 27/72

[52] U.S. Cl. .............................. 324/228; 73/86; 324/71.2; 324/226; 324/232; 324/238; 324/262

[58] Field of Search ...................... 324/71.2, 209, 324/226, 228–232, 234, 235, 238, 262, 220–221, 240–242; 73/862.08, 86

[56] References Cited

U.S. PATENT DOCUMENTS

| | | | |
|---|---|---|---|
| 2,467,306 | 4/1949 | Habig | 324/242 |
| 3,056,920 | 10/1962 | Herrald | 324/221 |
| 3,109,139 | 10/1963 | Branker | 324/240 |
| 4,379,261 | 4/1983 | Lakin | 324/232 X |
| 4,445,089 | 4/1984 | Harrison | 324/232 X |
| 4,866,383 | 9/1989 | Taliaferro | 324/228 |

*Primary Examiner*—Gerard R. Strecker
*Attorney, Agent, or Firm*—Jacob Shuster

[57] ABSTRACT

A magnetic field generator positioned externally of a non-ferrous metallic structure being examined, is rotated at a relatively low speed to produce a rotating magnetic field penetrating the metallic structure to a selected depth as a function of spacing between magnetic poles of the generator parallel to a planar surface of the metallic structure. Traction between the metallic structure and the magnetic field accompanying its rotation is measured. Corrosion of the metallic structure at subsurface depths is detected and quantified from such traction measurements.

9 Claims, 2 Drawing Sheets

5,532,589

SUBSURFACE EXAMINATION OF NON-FERROUS MATERIAL FOR DETECTING CORROSION BY MEASURING MAGNETIC TRACTION

BACKGROUND OF THE INVENTION

This invention relates in general to the detection of corrosion or the like within non-ferrous metallic structures.

The non-destructive testing of metallic structures for purposes of detecting corrosion thereof, is generally well known in the art. The detection of corrosion of pipelines for example, by computer processing of measurement data obtained from the pipeline wall surface, is disclosed in Ellmann et al. U.S. Pat. No. 4,909,091. Eddy current and ultrasonic measurement techniques are relied on for corrosion detection according to the Ellmann et al. patent. These techniques however limit corrosion detection to relatively shallow depths, and are rendered unsuitable by most coatings on surfaces of the materials being examined. Such coatings include paint, radar absorbing, sound absorbing and marine fouling materials. Tolerable coating thickness is furthermore limited by the "lift-off" effect of eddy current techniques, while ultrasonic techniques will not even tolerate thin layers of a porous coating or interfaces that produce extraneous reflections.

The use of a magnetic field generator to examine metallic products in order to detect material defects therein, is disclosed in Taliaferro U.S. Pat. No. 4,866,383. According to such Taliaferro patent, magnetic properties introduced into the product being examined when subjected to a magnetic field from the generator, cause relative movement between the product and generator sensed by a load cell attached to the generator. The technique disclosed in the Taliaferro patent is accordingly designed to differentiate between contaminants and other such defects within the product being examined.

It is therefore an important object of the present invention to provide a system and method for detecting and quantifying corrosion produced defects within a non-ferrous metallic structure at subsurface locations of substantial depth therein, especially when covered by a thick non-conductive coating.

An additional object of the invention in accordance with the foregoing object, is to provide a non-destructive method of examining a non-ferrous material by use of a generated magnetic field in order to detect corrosion of such material substantially below its external surface.

SUMMARY OF THE INVENTION

In accordance with the present invention, the magnetic field generated externally of a non-ferrous metal structure is rotated at a low rate adjacent to the surface of such structure about an axis perpendicular to such surface. The magnetic field accordingly penetrates the metal being examined to a depth that is a function of the distance between the opposite poles of the generator from which the magnetic field extends. Rotation of the magnetic field relative to the metal structure of test material being examined produces a traction thereon. Such traction is reduced by corrosion of the test material. As generally understood in the art, traction represents torsional resistance to relative movement between the rotating magnetic field and the surface of the test material. By measurement of such traction at a given rotational speed to accommodate magnetic field penetration to selected depths of the test material, data is obtained from which the corrosion is detected and quantified at such depths.

BRIEF DESCRIPTION OF DRAWING FIGURES

A more complete appreciation of the invention and many of its attendant advantages will be readily appreciated as the same becomes better understood by reference to the following detailed description when considered in connection with the accompanying drawings wherein.

DETAILED DESCRIPTION OF THE PREFERRED EMBODIMENTS

Figure 1:
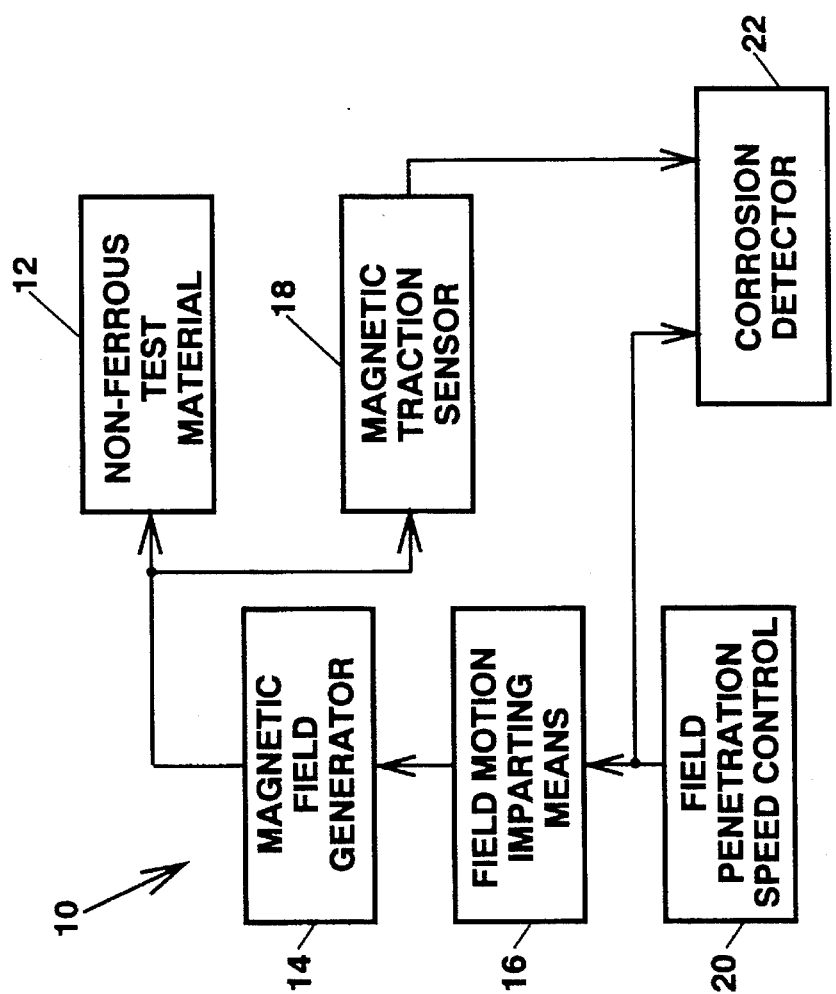
FIG. 1 is a block diagram of the corrosion detection system of the present invention.

Referring now to the drawing in detail, FIG. 1 diagrams a method generally denoted by reference numeral 10 for detecting subsurface corrosion of a non-ferrous, conductive material 12 to be tested, such as metals like aluminum, copper and brass referred to in Taliaferro U.S. Pat. No. 4,866,383 aforementioned. The test material 12 is penetrated by a magnetic field externally applied thereto by a generator 14 as hereinafter described. As explained in the Taliaferro patent, if the magnetic field produced by generator 14 moves relative to the test material 12 there will be a reaction tending to cause the material 12 to follow movement of the applied magnetic field. Electrical currents induced in the test material by the motion of the magnetic field applied thereto will produce traction according to a well known principle applicable to induction motors and magnetic brakes. Such traction on the test material 12 is accordingly produced by imparting rotational motion to the magnetic field generator 14 relative to the test material 12 at a relatively low speed corresponding to a predetermined penetration depth of the magnetic field in the material being tested, as denoted by diagram blocks 16 and 20 in FIG. 1, according to one embodiment of the invention. The resulting reaction between the magnetic field and the test material 12, referred to as magnetic traction, is measured by sensor 18 as also denoted in FIG. 1. Data on the selected rate of speed control 20, as well as the traction measurement data from sensor 18, is fed to a corrosion detector 22 for data processing purposes in order to assess corrosion of the test material 12 at various subsurface depths as a function of the traction measurement and geometrical factors associated with the rotating magnetic field interacting with the test material 12. Such corrosion detector 22 may be associated with imaging technology well known in the art through which the processed data is utilized to map corrosion thickness variation for a test object.

Figure 2:
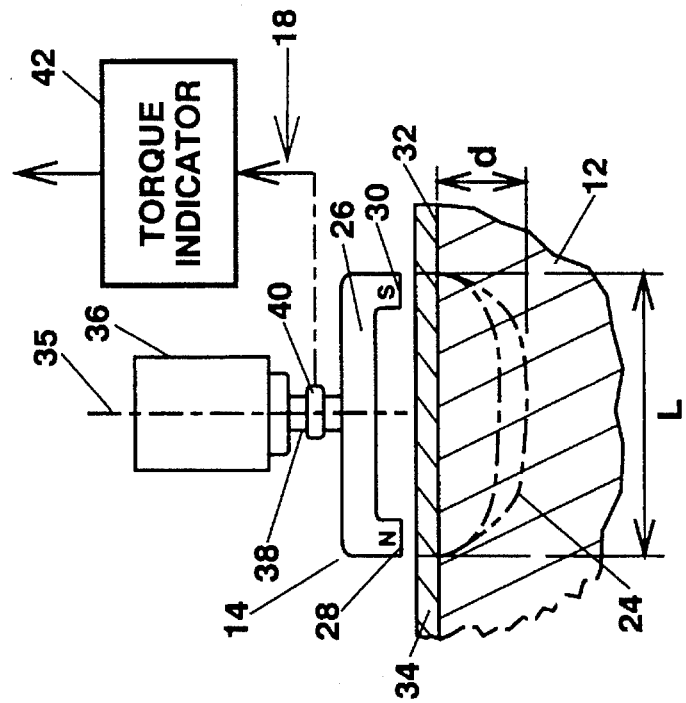
FIG. 2 is a partial side view of the magnetic field generator and traction sensor portions of the system depicted in FIG. 1, pursuant to one embodiment of the invention.

The geometric factors associated with the rotating magnetic field 24 are depicted in FIG. 2, corresponding to one embodiment of the invention. In such illustrated embodiment, the magnetic field generator 14 is in the form of a permanent magnet 26 having opposite magnetic poles 28 and 30 aligned with a plane parallel to a continuous, planar portion of a surface 32 of the test material 12 as shown and fixedly spaced therefrom by a magnetically transparent cover 34. The penetration depth (d) of the magnetic field 24 as diagrammed in FIG. 2, is a function of the spacing between poles 28 and 30. Accordingly, the pole spacing distance (1) basically determines the magnetic field penetration depth (d) as long as the permanent magnet 26 is rotated at its relatively low speed. Such rotation of magnet 26 about an axis 35 perpendicular to and intersecting the surface 32 is imparted by an electric motor 36 through a shaft 38 on which a suitable torque sensing device 40 generally known in the art is mounted. The output of sensing device 40 is fed to an indicator 42 of the traction measuring sensor 18. Thus, traction measurement is obtained in terms of torque exerted on magnet 26 according to the embodiment depicted in FIG. 2.

Figure 3:
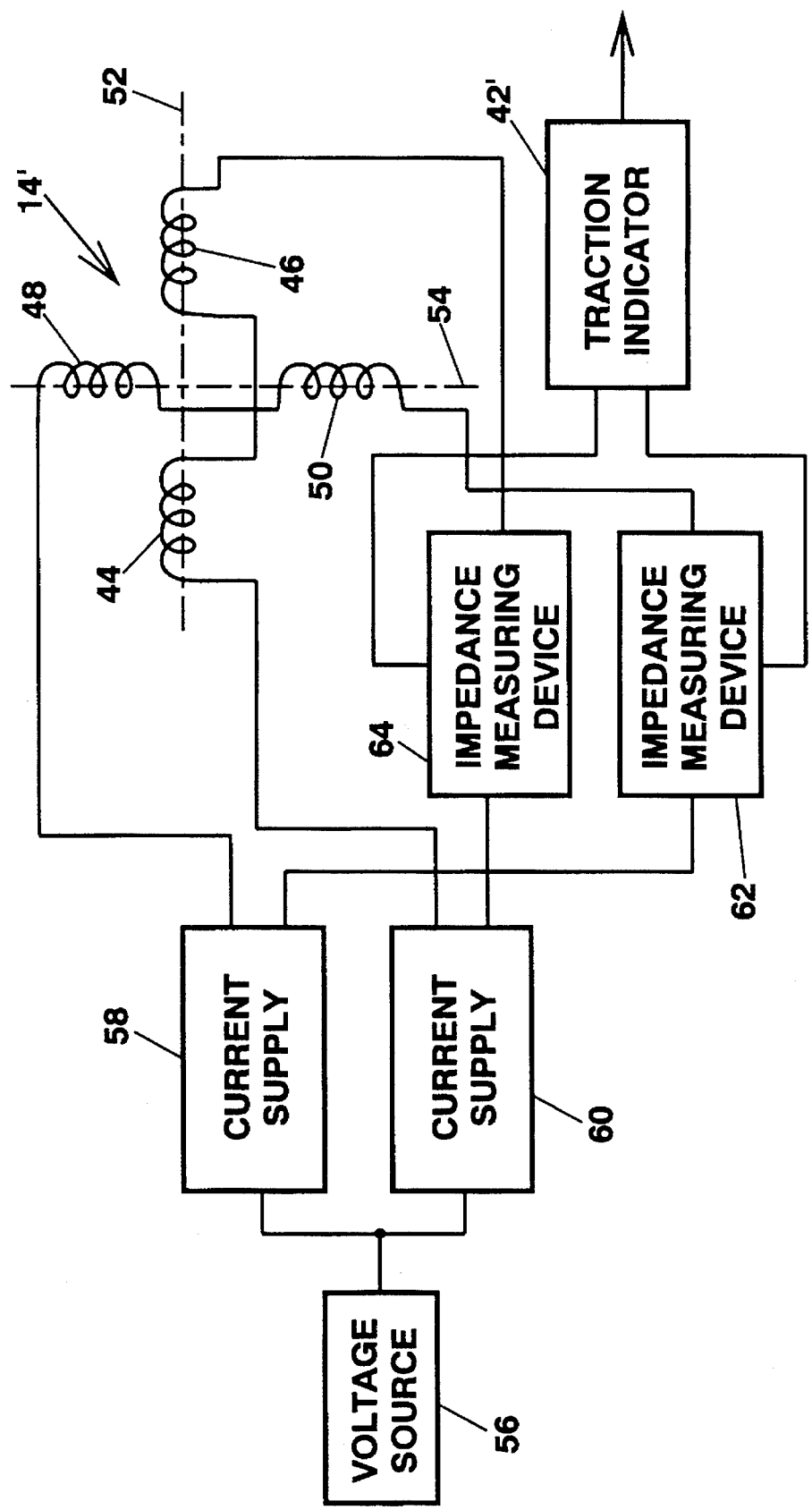
FIG. 3 is schematic diagram of the magnetic field generator and traction sensor components of the system, pursuant to another embodiment of the invention.

According to another embodiment as diagrammed in FIG. 3, the magnetic traction sensor generally referred to by reference numeral 18' is associated with a magnetic field generator 14' having two pairs of magnetic induction coils 44, 46 and 48, 50. One pair of coils 44 and 46 are positioned in spaced alignment with each other to produce a magnetic field extending between poles spaced along axis 52 parallel to the surface of the test material 12 being assessed. The other pair of coils 48 and 50 are arranged to produce a magnetic field extending between poles along an axis 54 perpendicular to axis 52 as shown in FIG. 3. Each pair of coils is connected to a voltage source of electrical energy 56 through a sinusoidal current supply 58 or 60. The current supplies 58 and 60 respectively vary the electrical currents sinusoidally in each pair of coils in out-of-phase time spaced relation to each other to thereby effect rotation of the magnetic field which penetrates the test material 12, as hereinbefore described with respect to FIG. 2. Such use of magnetic field generating induction coils is per se generally known in the art, as for example in electrical induction motors.

The magnetic field traction measurements of sensor 18' diagrammed in FIG. 3, is obtained from the driving point impedances of each pair of induction coils through impedance measuring devices 62 and 64 connected to traction indicator 42'. Thus, the traction sensor output of indicator 42' of traction sensor 18' reflects the affect of the metallic structure of test material 12 and its angular orientation on the rotating magnetic field of generator 14'.

It will be apparent from the foregoing description that the output of the traction sensor 18 or 18' and data from the speed control 20, as diagrammed in FIG. 1, when fed to the corrosion detector 22 forms the basis for data processing analysis of magnetic field behavior at different depths of the test material 12. For example, the orientation of cracks and fibers in the metallic structure of the test material caused by corrosion would be readily detected and quantified from torque data received from sensor 18 or the inducted current in the induction coils resulting from angular dependence of the accompanying traction in terms of ratio of voltage/current measurements of sensor 18' as the magnetic field rotates.

Obviously, other modifications and variations of the present invention may be possible in light of the foregoing teachings. It is therefore to be understood that within the scope of the appended claims the invention may be practiced otherwise than as specifically described.

What is claimed is:

1. A method of examining a non-ferrous conductive material for presence of other subsurface material therein, involving relative movement between the conductive material and a penetrating magnetic field generated externally of the conductive material, comprising the steps of: selectively imparting movement to the magnetic field relative to the conductive material; measuring traction resulting from motion of the magnetic field and detecting the presence of said other subsurface material within the conductive material as a function of the measured traction and the motion of the magnetic field, the magnetic field being generated by a permanent magnet having polar ends at which opposite magnetic poles are located.

2. The method as defined in claim 1 wherein said step of selectively imparting the relative movement to the magnetic field is performed by rotation of the magnetic field.

3. The method as defined in claim 1 wherein said magnetic field is established between the opposite magnetic poles in a direction parallel to a planar surface of the conductive material from which said subsurface penetration of the magnetic field extends to a depth that is a function of distance between the opposite magnetic poles.

4. The method as defined in claim 2 wherein said step of measuring the traction is performed by measuring torque imparted to the permanent magnet during said rotation of the magnetic field.

5. The method as defined in claim 1 wherein said step of selectively imparting the relative movement to the magnetic field is performed by rotation of the permanent magnet at a predetermined speed; and said step of sensing the traction is performed by measuring torque imparted to the permanent magnet during said rotation thereof at said predetermined speed.

6. The method as defined in claim 5, wherein the magnetic field penetrates the conductive material to a depth that is a function of distance between the opposite magnetic poles of the permanent magnet in a direction parallel to a planar surface of the test material during said rotation of the permanent magnet at the predetermined speed.

7. A method of assessing subsurface corrosion of a non-ferrous metal comprising the steps of generating a magnetic field externally of the metal for penetration underlying a continuous surface portion thereof; imparting rotation to the magnetic field about an axis intersecting said continuous surface portion of the metal; sensing magnetic traction resulting from the rotation imparted to the magnetic field during said penetration of the metal and detecting said subsurface corrosion underlying said continuous surface portion of the metal as a function of the magnetic traction sensed.

8. The method as defined in claim 7 wherein said magnetic field extends between magnetic poles of opposite polarity aligned parallel to continuous surface portion of the metal from which said penetration occurs to a predetermined depth as a function of distance between said poles.

9. In a method for detecting defects in a metallic product having a test surface penetrated by a magnetic field during rotation thereof about an axis intersecting the test surface and wherein measurement of traction between the test surface and the magnetic field resulting from said rotation thereof is obtained; the improvement residing in: locating the magnetic field during said rotation thereof over a continuous portion of the test surface; and extracting data from said measurement of the traction which reflects presence of corrosion underlying the continuous portion of the test surface as the defects being detected.

* * * * *